United States Patent
Rueckert et al.

(10) Patent No.: US 9,488,649 B2
(45) Date of Patent: Nov. 8, 2016

(54) IMAGING METHOD USING MAGNETIC SMALL PARTICLES AND CORRESPONDING DEVICE

(75) Inventors: Martin Rueckert, Wuerzburg (DE); Volker C. Behr, Gerbrunn (DE)

(73) Assignees: Martin Rückert, Würzburg (DE); Volker C. Behr, Gerbrunn (DE)

( * ) Notice: Subject to any disclaimer, the term of this patent is extended or adjusted under 35 U.S.C. 154(b) by 614 days.

(21) Appl. No.: 13/638,624

(22) PCT Filed: Apr. 1, 2011

(86) PCT No.: PCT/EP2011/001651
§ 371 (c)(1),
(2), (4) Date: Dec. 11, 2012

(87) PCT Pub. No.: WO2011/120713
PCT Pub. Date: Oct. 6, 2011

(65) Prior Publication Data
US 2013/0079623 A1    Mar. 28, 2013

(30) Foreign Application Priority Data
Apr. 1, 2010 (DE) .......... 10 2010 013 900

(51) Int. Cl.
*A61B 5/05* (2006.01)
*G01N 33/569* (2006.01)
(Continued)

(52) U.S. Cl.
CPC .......... *G01N 33/569* (2013.01); *A61B 5/0035* (2013.01); *A61B 5/055* (2013.01);
(Continued)

(58) Field of Classification Search
CPC ............. G01N 33/566; G01N 33/553; G01N 33/569; A61B 5/055; A61B 18/22
See application file for complete search history.

(56) References Cited

U.S. PATENT DOCUMENTS 7,619,408 B2 * 11/2009 Gleich ................ A61B 5/0515
                                                          324/204
7,747,304 B2     6/2010 Gleich
(Continued)

FOREIGN PATENT DOCUMENTS

WO    WO2004091386 A2    10/2004
WO    WO2004091390 A2    10/2004
(Continued)

OTHER PUBLICATIONS

International Search Report and Written Opinion; Mailed on Aug. 29, 2011 for corresponding PCT/EP2011/001651.
(Continued)

*Primary Examiner* — Joel Lamprecht
(74) *Attorney, Agent, or Firm* — Mendelsohn Dunleavy, P.C.; Steve Mendelsohn

(57) ABSTRACT

The invention relates to a method for imaging from a distribution of small magnetic particles. According to said method, the magnetisation of the small particles is rotated asynchronously to the magnetic field by means of an outer magnetic field of suitable field intensity and rotational frequency, which rotates about a longitudinal axis (z), whereby an asynchronous average rotational frequency is generated for a set of particles according to the field intensity; a spatial dependence is impressed on each set of particles by means of a magnetic gradient field of the asynchronous average rotational frequency; the frequency parts of the superpositioned transverse magnetisation (MQ) of the set of particles are detected; and a spatially resolved distribution of the transverse magnetisation (MQ) determines the small particles and emits same by means of the frequency parts. The invention also relates to a suitable device (1). An improved spatial resolution can be obtained, compared to the previous magnetic particle imaging methods, with essentially lower field intensities.

20 Claims, 2 Drawing Sheets

(51) Int. Cl.
*A61B 5/055* (2006.01)
*G01N 33/543* (2006.01)
*G01R 33/12* (2006.01)
*A61B 5/00* (2006.01)
*C12Q 1/04* (2006.01)
*G01N 33/68* (2006.01)

(52) U.S. Cl.
CPC ............ *A61B 5/0515* (2013.01); *C12Q 1/04* (2013.01); *G01N 33/54326* (2013.01); *G01N 33/5695* (2013.01); *G01N 33/56983* (2013.01); *G01N 33/6854* (2013.01); *G01R 33/1269* (2013.01)

(56) References Cited

U.S. PATENT DOCUMENTS

| | | | |
|---|---|---|---|
| 7,994,786 | B2 | 8/2011 | Weaver et al. |
| 8,305,076 | B2 * | 11/2012 | Sack et al. .................... 324/309 |
| 8,532,735 | B2 | 9/2013 | Gleich |
| 2004/0033627 | A1 | 2/2004 | Aytur et al. |
| 2006/0189868 | A1 | 8/2006 | Gleich et al. |
| 2006/0211938 | A1 | 9/2006 | Gleich et al. |
| 2006/0211941 | A1 | 9/2006 | Gleich |
| 2006/0248944 | A1 | 11/2006 | Gleich et al. |
| 2008/0220411 | A1 | 9/2008 | McNaughton et al. |
| 2008/0309330 | A1 | 12/2008 | Ohyu et al. |
| 2010/0066363 | A1 | 3/2010 | Brazdeikis et al. |
| 2010/0179412 | A1 | 7/2010 | Weizenecker et al. |

FOREIGN PATENT DOCUMENTS

| | | |
|---|---|---|
| WO | WO2004091408 A2 | 10/2004 |
| WO | WO2008099331 A1 | 8/2008 |
| WO | WO2009008956 A2 | 1/2009 |
| WO | WO2009037636 A1 | 3/2009 |
| WO | WO2010041178 A1 | 4/2010 |

OTHER PUBLICATIONS

English Translation of the International Preliminary Report on Patentability and Written Opinion; Mailed on Oct. 11, 2012 for corresponding PCT/EP2011/001651.

Weizenecker, J., et al., "Three-Dimensional Real-Time in Vivo Magnetic Particle Imaging," Physics in Medicine and Biology; 2009, vol. 54, pp. L1-L10.

Biederer, S., et al., "A Spectrometer for Magnetic Particle Imaging," IFMBE Proceeding 2008, vol. 22, pp. 2313-2316.

Weizenecker, J., et al., "A Simulation Study on the Resolution and Sensitivity of Magnetic Particle Imaging," Physics in Medicine and Biology; 2007, vol. 52, pp. 6363-6374.

Carr, H. Y., et al.; "Effects of Diffusion on Free Precession in Nuclear Magnetic Resonance Experiments"; Physical Review, vol. 94, No. 3; May 1, 1954; pp. 630-638.

* cited by examiner

IMAGING METHOD USING MAGNETIC SMALL PARTICLES AND CORRESPONDING DEVICE

The invention relates to a new imaging method using magnetic small particles. The invention furthermore relates to a device suitable for carrying out this method.

A method of the type mentioned in the introduction, also referred to as "magnetic particle imaging", and a device suitable for carrying it out, are known from the article "Tomographic Imaging Using the Non-Linear Response of Magnetic Particles", Bernhard Gleich, Jürgen Weizenecker, Nature, Vol. 435, Jun. 30, 2005. In this article, the nonlinear relationship between the magnetization of a ferromagnetic small particle in relation to an external magnetic field is used for spatial imaging of the given distribution of the small particles. To this end, in particular, use is made of the fact that the magnetization reaches a saturation value in strong magnetic fields, while there is a substantially linear dependency on the field strength in a range around the zero point of the field strength. If the external magnetic field is varied sinusoidally around the zero point, then a square-wave function results owing to the saturation effect as a response function of the magnetization. When transformed into the frequency domain, the magnetization signal is therefore composed of a sum of the harmonics of the fundamental frequency of the applied magnetic field. The signal of the magnetization, for example acquired inductively, can therefore easily be separated from the applied excitation signal by separating off the fundamental frequency component.

For position encoding, a strong magnetic gradient field with a field-free point at the measurement volume is generated in the examination region. Since the magnetization of the small particles reaches its saturation value outside the field-free point, only those small particles which lie at the field-free point effectively contribute to the imaging. By displacing the field-free point over the examination region, the number of magnetic small particles respectively located there can be determined by means of the amplitude of the received magnetization signal. The field-free point may in this case be moved either by an actual movement of the measurement apparatus or by appropriate driving of the gradient field, also referred to as a selection field.

By the known method for imaging by means of magnetic small particles, a distribution of the magnetic small particles can be observed in a position-resolved fashion both in vitro and in vivo. By using a contrast agent containing magnetic small particles, it is therefore possible to obtain spatial recordings of tissues, organs or a vascular system. Is also possible to observe metabolic processes by the magnetic small particles adhering, for example, to specific organic molecules participating in metabolic processes. It is likewise possible to provide the magnetic small particles with functional groups which couple to specific body cells, so that conclusions can be drawn from their distribution. By means of time resolution of the distribution of the contrast agent, it is also possible to image or represent dynamic processes, for example the blood flow through an organ, etc.

The spatial resolution achievable with the known method is set by the necessary gradient of the selection field. The spatial resolution is commensurately better when the gradient of the selection field is selected to be greater. For magnetic small particles with a diameter of a few tens of nm, typical gradients of around 5 T/m (tesla per meter) or more are required, in order to achieve a spatial resolution in the submillimeter range. Such high gradient fields, however, can in practice only be achieved with superconducting coils or by means of neodymium magnets, which disadvantageously increases the costs of such imaging significantly. For comparison, typical gradient fields known from nuclear magnetic resonance methods range around 100 mT/m.

Furthermore, a higher spatial resolution of the known method is associated with a deterioration of the signal-to-noise ratio. This is because when the gradient of the selection field is selected to be steeper, the region of linear response of the magnetization of the small particles is commensurately smaller and commensurately fewer small particles contribute overall to the measurement signal.

It is an object of the invention to provide a method for imaging by means of magnetic small particles and a device suitable therefor, with which an improved spatial resolution can be obtained in comparison with the prior art and the production of which entails lower costs.

This object is achieved in relation to the method according to the invention in that by means of an external magnetic field of suitable field strength and suitable rotation frequency rotating about a longitudinal axis, the magnetizations of the small particles are set in a rotation which is asynchronous with respect to the magnetic field, by means of which an asynchronous average rotation frequency with respect to the field strength results for a particle ensemble, in that a position dependency is imposed by means of a magnetic gradient field with the asynchronous average rotation frequency of the respective particle ensemble, in that the frequency components of the superimposed transverse magnetization of the particle ensemble are recorded and in that spatially resolved distribution of the transverse magnetization is determined by means of the frequency components and is output.

The invention in this case surprisingly departs from the approach previously adopted by the specialist field, which uses the nonlinear relationship of the magnetization with an external magnetic field for imaging by means of magnetic small particles. Instead, for imaging the invention uses the fact that the rotation of the magnetic small particles or of their magnetization in an external rotating magnetic field is decomposed as a function of the field strength and rotation frequency into a region of synchronous rotation and a region of asynchronous rotation. In the case of a mechanically rotating small particle, this depends on friction terms in relation to the environment. If the magnetization rotates in the crystal lattice of the small particle, then other friction terms are responsible. If the torque transmitted by the external magnetic field is too small compared with the friction terms then the magnetization, or the small particle, lags behind the rotation of the magnetic field since it has a tendency to remain stationary relative to the environment. This results in a nonlinear fluctuation of the rotation of the magnetization relative to the rotation of the magnetic field. On average, a measurable rotation drift then occurs.

According to US 2008/0220411 A1, the magnetization of the small particle rotates on average synchronously with the rotation of the magnetic field up to a critical frequency $\Omega_C$, as a function of the field strength of the external magnetic field. If the rotation frequency of the magnetic field exceeds the critical rotation frequency $\Omega_C$, then the magnetization of the small particle rotates asynchronously with a reduced average rotation frequency. This average asynchronous rotation of the magnetization can be observed as a frequency term of the magnetization. This profile of the average rotation frequency of the magnetization of the small particle can be seen in FIG. 1. For a lower field strength, there is a lower critical average rotation frequency $\Omega_C$ than for a higher field strength. This can be inferred from the curve profiles a and b represented in FIG. 1. The relationship between critical average rotation frequency $\Omega_C$ and the field strength B of the external magnetic field is in this context given by:

$$\Omega_c = \frac{mB}{\gamma}.$$

Here, m denotes the magnetic moment of the small particle. The term γ describes a friction term which in the case of a mechanical rotation of the small particle involves the viscosity of the environment and a form factor of the small particle. In the case of a rotation of the magnetization in the crystal lattice of the small particle, the friction term γ is to be determined empirically.

The invention now recognizes for the first time that the asynchronous rotation of the magnetization of the small particles can be used for imaging, since in this case the recordable frequency of the magnetization rotating relative to the external magnetic field is different to the frequency of the excitation field. To this extent, the average rotation frequency of the magnetization can be separated easily in terms of measurement technology from the frequency of the excitation field. In a particle ensemble, the corresponding frequency term can be determined by recording the superimposed transverse magnetization (with respect to the longitudinal axis, about which the external magnetic field rotates). This may, for example, be done inductively using a suitable measurement coil.

For imaging and therefore for spatial resolution, the above-described fact is furthermore used that the critical rotation frequency $\Omega_C$ is dependent on the field strength of the external magnetic field. This offers the possibility of carrying out position encoding in a similar way to the nuclear magnetic resonance method by applying a magnetic gradient field. According to FIG. 1, with an equal rotation frequency of the magnetic field, a respectively different average asynchronous rotation frequency of the magnetization of the small particles is set as a function of the external field strength. Position information is therefore imposed on the average asynchronous rotation frequency of the magnetization of the small particles, and this is used for the imaging.

If a magnetic gradient field is generated along a predetermined axis or spatial direction, then the observed asynchronous rotation of the superimposed transverse magnetization is decomposed into strips of equal frequencies perpendicular to this axis. By recording the signal intensities, respectively allocated to the frequencies, a projection of the distribution of the superimposed transverse magnetization onto the axis of the gradient field is generated. This corresponds to imaging, spatially resolved in one dimension, by means of the distribution of the magnetic small particles or by means of the distribution of their transverse magnetization. The magnetic gradient field is therefore used for position encoding by means of the frequency distribution which is set up. This possibility is therefore also referred to below as a frequency encoding method.

On the other hand, the average asynchronous rotation frequency of the magnetization of the small particles is influenced by the chemical environment. In a similar way to the nuclear magnetic resonance method, a so-called chemical shift is formed in the observed rotation frequency. This can likewise be made visible by the method provided. To this end, the method is repeated with different magnetic gradient fields, by means of which the regions of different chemical environment are sampled. By means of the measurement information obtained, an image can be generated by means of the spatial distribution of the environmental parameters of the small particles. Since in particular the viscosity involved in the friction term is temperature-sensitive, this method can for example be used to visualize temperature gradients, particularly in metabolic processes etc.

It is also possible to impose a position-dependent phase angle on the particle ensemble by means of a gradient field switched on for a predetermined time period, and to use this phase angle for the imaging. This is because, for as long as the magnetic gradient field is switched on, the individual magnetic small particles rotate position-dependently with respectively different asynchronous rotation frequencies, so that after switching off there is a position-dependent phase angle which can likewise be employed to measure a position-resolved distribution. The gradient field is used before the measurement per se for position encoding by means of the phase angle which is set up. This possibility is also referred to below as a phase encoding method.

Compared with the known nuclear magnetic resonance method, the present invention offers the enormous advantage that a static polarization field for alignment is not required. Rather, the magnetic small particles are manipulated directly by the magnetic rotation field. While field strengths of about 1.5 T are required for alignment of the nuclear spins, in order to be able to utilize about 3 ppm of the proton spins present for the signal generation, field strengths of between 0.1 and 100 mT are sufficient in order to generate an asynchronous rotation with from about 0.1% to 100% of the existing magnetization of the small particles. While the polarization field can only be generated with expensive superconducting coils in the case of nuclear magnetic resonance, in order to be able to achieve an image quality compatible with routine clinical use, the magnetic rotation field for visualizing the rotating magnetization of the small particles can be generated with favorable air coils or water-cooled coils.

In the nuclear magnetic resonance method, furthermore, the measurement signal can only be generated by applying a radiofrequency magnetic field with the Lamor frequency of about 60 MHz. In contrast to this, in the method described here a rotating magnetic field with a frequency of between 1 kHz and 1 MHz is sufficient for generating the measurement signal. In the simplest case, a separate gradient coil for generating the gradient field is not even necessary. This is because the gradient field necessary for the imaging can be set by appropriate driving of the coils generating the rotating magnetic field.

In order to generate the field strengths necessary in this case, simple air coils are in fact sufficient, which can be operated with currents of from 1 to 100 A. Such currents, as well as the frequencies of up to 1 MHz provided here, can be handled with conventional and known power electronics. Compared with the nuclear magnetic resonance method, the method of magnetic particle imaging described here is to this extent associated with enormous cost advantages. These enormous advantages, based on the large differences of the necessary field strengths, are due to the fact that the nuclear spin of a hydrogen atom is not observed, but instead the single large total spin resulting from the coupling of the electron spins of the atoms in the magnetic nanoparticles is measured. The resulting magnetic moment in a magnetite particle measuring about 25 nm is, for example, 10 million times greater than that of the hydrogen proton. Although the present method is broadband compared to the nuclear magnetic resonance method, this disadvantage is nevertheless more than compensated for by the enormously greater magnetization.

Compared with the previously adopted approach of magnetic particle imaging by observing the nonlinear relationship of the magnetization in relation to a strong external magnetic field, the method described here additionally has a substantially improved signal-to-noise ratio. In the previously known method according to the article by Gleich and Weizenecker, a measurement signal is generated sequentially only at the field-free point of the applied magnetic selection field. For a higher spatial resolution, the volume of this signal-generating region is reduced owing to the increased gradient. In a two-dimensional representation, the signal-to-noise ratio increases with an increasing resolution proportionally to $1/N$, and in a three-dimensional representation proportionally to $1/N^3$, where N is the number of image points in a dimension.

While conventional magnetic particle imaging examines a single-voxel excitation in each individual measurement step (volume at the field-free point), with the new method described here a signal from the entire sample volume is recorded with each individual measurement. For this reason, moreover, the signal-to-noise ratio increases with the number of measurement steps. The advantage thereby achieved over known magnetic particle imaging is particularly dramatic in three-dimensional imaging. If a three-dimensional image matrix comprising 64×64×64 image points is examined, for example, this gives a 512 times increased signal-to-noise ratio of the new method compared with the previously known technology. If one wished to achieve a 512 times higher signal-to-noise ratio by averaging, it would be necessary to average more than 26000 times. The signal bandwidth, which is in turn lower in comparison with conventional magnetic particle imaging, furthermore allows the design of correspondingly adapted receiver tuned circuits.

The new type of method proposed here for magnetic particle imaging offers the further advantage that imaging methods known from the nuclear magnetic resonance method can be carried out adequately. For example, the rotating magnetizations can be brought into synchronous rotation, and therefore in phase, by a stronger rotating magnetic field or by reducing its frequency, which as it were corresponds to the 90° spinflip of nuclear magnetic resonance, which is required in each fundamental measurement sequence of nuclear spin tomography in order to generate a measurable magnetization component. The degree of the reduction of the superimposed transverse magnetization is then a measure of the so-called transverse relaxation, which describes the convergence of the individual magnetizations due to the already described environmental parameters, field inhomogeneities or particle variations. In a similar way to the spin echo known from the nuclear magnetic resonance method, the individual magnetizations can be brought back in phase by reversing the rotation direction of the external magnetic field. This corresponds as it were to a 180° spinflip, as is used to generate the spin echo in nuclear magnetic resonance.

As magnetic small particles, ferromagnetic or superparamagnetic particles are used, which have as great as possible a magnetic moment in relation to their volume. For use in biology and medicine, nanoparticles having particle diameters of between 20 and 200 nm are suitable in particular. The greater the ratio between the magnetic moment and the volume is, the higher is the rotation drift in relation to the external magnetic field in the case of asynchronous rotation.

The rotation diffusion and the scatter of the particle properties lead as described above to dephasing of the particles, so that the magnetization is abated on average. The present method is therefore in the end limited only by the rotation diffusion, since this limits the correlation of the angle orientation of the small particles with one another. In order to be able to expediently implement the concepts of frequency and phase encoding known from nuclear spin tomography, the condition $mB > \sqrt{2D}$ should preferably be satisfied. Here, D denotes a diffusion constant which, for mechanical rotation of the small particles, is given in particular by the viscosity and, in the case of rotation of the magnetization in the crystal lattice, is in turn obtained empirically. The former case is referred to as a so-called Brown relaxation. The latter case is referred to as Néel relaxation. The inequality given is a measure of the achievable separating sharpness of the frequency or phase encoding. The greater mB is, the smaller is the resulting line broadening in the signal spectrum.

In the case of mechanical rotation of the small particle, the viscosity of the surrounding liquid can be observed by means of the rotation drift, or in the case of a medical use increased friction with vessel or cell walls can be observed. Since temperature differences can be inferred by a different viscosity, the temperature inside a medium can also be measured by means of the viscosity. If the small particles are used as probes, on the surface of which molecules accumulate, the hydrodynamic particle diameter of the small particle is increased and the rotation drift is correspondingly reduced. For this reason, molecule concentrations can be localized and quantified by means of the rotation drift shift.

If, however, the small particles accumulate on cell surfaces, the Brown relaxation is suppressed almost fully so that only the Néel relaxation remains. Depending on the particle type, the relaxation time can therefore vary by several orders of magnitude. In the case of magnetite nanoparticles having an average diameter of about 25 nm, this leads to a variation of the relaxation time from about 5 microseconds to about 1 millisecond.

The magnetic coupling of clustered small particles, for example due to crosslinking via functional groups or agglomeration in cell vesicles, likewise varies the rotation drift and can be detected thereby.

Advantageously, a magnetic gradient field for frequency encoding of the position information is generated during the recording of the frequency components of the transverse magnetization. During the measurement of the transverse magnetization, a frequency spectrum is recorded in which a spatial coordinate along the gradient field is allocated to each frequency. The spatial resolution is in this case given by the achievable spatial variation of the rotation drift. The product of switch-on time and gradient strength should preferably be selected so that, over the shortest distance which is intended to be resolved, the orientation of the magnetization differs over this distance by at least one full rotation at the end of the measurement.

Field inhomogeneities, the scatter of the particle properties and local variations in relation to the chemical environment, the viscosity or the like cause spectral broadening which limits the position encoding by means of frequency allocation. If the scatter of the particle properties is too great, or if one or more of the other parameters mentioned, such as the viscosity or the temperature or molecule concentrations are additionally intended to be interrogated by means of the frequencies of the asynchronous rotation, the frequency encoding cannot be employed unrestrictedly for the position encoding.

This limitation can be overcome by supplementing the frequency encoding with phase encoding steps, or fully replacing it by phase encoding. Advantageously, therefore, a magnetic gradient field is generated for a predetermined time period in particular before recording the frequency components of the transverse magnetization, in order to generate phase encoding in the particle ensemble.

If the measurement signal is recorded after the phase encoding, each location has experienced a phase shift corresponding to the position in the selected gradient and its strength. In particular, for example, N steps each with an increase of the gradient strength by 1/N of the maximum possible gradient strength provides information making it possible to calculate back to the distribution of the transverse magnetization at N coordinates from a position-dependent phase shift or phase angle. This is preferably carried out by means of a fast Fourier transform (FFT).

The transverse magnetization may in principle also be recorded during the phase encoding steps. The data obtained in this way, however, cannot be allocated to a Cartesian-ordered Fourier space, from which the desired spatial distribution could be calculated directly by a Fourier transform. Rather, the data provide complementary information and can only be evaluated separately and therefore elaborately.

If the image encoding is carried out fully by phase encoding, then N×N×N measurement steps are required for 3 dimensions each with N coordinates. In this case the frequency distribution, which is in particular subsequently recorded after each step without a gradient field, provides entirely redundant information which primarily reflects the distribution or scatter of the rotation properties of the small particles. This distribution is in this case obtained separately for each of the N×N×N spatial points. Since this distribution can be measured independently, a position distribution of the environmental parameters, for example the temperature, can be inferred from the shift of this frequency distribution.

After the phase encoding, of course, a magnetic gradient field for frequency encoding may again be applied, for example so as to obtain position encoding in the other spatial direction. This is suitable when only the density distribution of the small particles is interrogated and when, as mentioned, the variation of the particle properties is sufficiently small.

Instead of fully replacing the frequency encoding by phase encoding, the encoding may accordingly also be carried out only partly by phase encoding and partly by frequency encoding. The number of the additionally required subdivision of the frequency encoding into phase encoding steps is given, for example, by the respective width of the particle scatter, or the spectral broadening resulting therefrom.

The imaging of a spatial distribution of the particle ensemble differs in relation to the imaging of a spatial distribution of the environmental parameters in that the frequency encoding is employed once for the spatial resolution, and the existing frequency distribution is used once for recording the variation imposed by the environment. In the former case, the position encoding of the frequencies is switched on during the measurement of the gradient. In the latter case, the signal recording takes place without a gradient switched on.

In an expedient configuration, after the magnetic gradient field is switched off, a second equal magnetic gradient field of opposite sign is generated with the same time period, wherein the spatially resolved distribution of the transverse magnetization is subsequently determined in a plane perpendicular to the profile of the gradient and is output. This method makes it possible to carry out spatial measurement of flow profiles or vessel structures.

In this case, a magnetic gradient is first applied for a prespecified time period in a predetermined spatial direction, in which the flow is intended to be measured. Subsequently, the same gradient is applied with the same gradient strength for the same time period, but with an opposite sign. In a plane perpendicular to the gradient, the spatial image encoding takes place as already described, for example by means of suitable frequency encoding and/or phase encoding. The frequency distribution of the transverse magnetization is recorded. The effect of the first two steps is that unmoved small particles do not experience a phase change, since the second step makes the first step substantially reversible for stationary particles. Particles moving in the direction of the gradient, however, experience a phase change which is proportional to the distance travelled. The phase change is therefore a measure of the flow rate.

In order to be able to carry out a flow measurement even with particles having a large scatter of the rotation properties, combination with a 180° spinflip is advantageous. After a refocusing pulse, to be explained below, for "phase equalization" of the particle ensemble, the first two steps are carried out once before and once after a reversal of the rotation direction of the magnetic rotation field. This gives an echo signal which, in the case of stationary particles, occurs at exactly double the time between the refocusing pulse and the rotation direction reversal.

The small particles, which have in the meantime become out of phase owing to the particle properties, rotate in phase again after the rotation direction reversal, which results in an echo signal, again increased in intensity, of the superimposed transverse magnetization. If the small particles or the particle ensemble move in the direction of the gradient, then this echo signal is shifted proportionally to the speed, any influence due to particle scatter being neutralized.

In a preferred refinement of the method provided, a magnetic gradient field is generated by spatial variation of the field strength of the rotating magnetic field. The rotating magnetic field may, for example, be generated by means of coil pairs distributed in the circumferential direction, which are driven appropriately. In the simplest embodiment, the rotating magnetic field may be generated by means of a pair of Helmholtz coils oriented orthogonally to one another. To this end, the Helmholtz coil pairs are correspondingly driven sinusoidally. By means of modified driving, an additional gradient field for position encoding may also be generated by means of these coils. In the simplest case, accordingly, a separate gradient coil is not required for generating the magnetic gradient field.

In an additional or alternative configuration, the gradient field is generated not by a variation of the field strength of the rotating magnetic field, but by superimposing a homogeneous rotation field with a static, spatially varying offset field. The latter is generated, for example, by separate gradient coils.

By means of the magnetic gradient field, a position dependency is imposed on the average asynchronous rotation of the individual magnetizations and therefore, in particular, of the measurable superimposed transverse magnetization. This may—as already described—be used directly for one-dimensional spatial imaging of the corresponding distribution of the small particles. In order to be able to localize and correspondingly image environmental parameters, chemical changes, etc., in a particular embodiment the described method is repeated, the frequency components of the transverse magnetization being recorded several times for different gradient fields. As a result of this, the asynchronous rotation frequencies can be localized, correspondingly analyzed and used for imaging.

In another preferred configuration, a first gradient field is generated along a first direction in a first step for a time period, a second gradient field is generated along a second direction in a second step, the frequency distribution of the transverse magnetization is recorded in a third step, the aforementioned steps 1 to 3 are repeated with a number of modified first gradient fields in a fourth step, and a two-dimensional distribution of the transverse magnetization is determined from the set of measurement signals obtained and is output.

In this method of two-dimensional representation, the frequency space is scanned with system of Cartesian coordinates. At the start of the measurement, a phase characteristic is imposed on the magnetization of the small particles by means of the first gradient field along the first direction, by applying the first gradient field for a predetermined time over the measurement volume. The transverse magnetization preimposed in this way is then projected onto the second direction by means of a second gradient field.

The repetition of this measurement sequence with different prephasing by varying the first gradient field then delivers a set of measurement signals which corresponds to a hologram. By a two-dimensional Fourier transform, the desired spatial distribution of the magnetization can then be obtained directly. This allows direct image reconstruction with the aid of a two-dimensional "fast Fourier transform" (FFT) within an extremely short time.

If the second gradient field is not switched on for frequency encoding during the measurement, but instead used in preceding phase encoding, then as already described a spatial distribution of the environmental parameters can be obtained. In this case, the first and second gradient field may also be applied simultaneously, since the effect of the gradients is superimposed almost linearly on the phase.

If, in this method, the first and second gradient field are used for phase encoding before the measurement and a third gradient field is used for frequency encoding during the measurement, then the first two first gradient fields encode two spatial directions by means of the phase and the third gradient field encodes the third spatial direction by means of the frequency. This then corresponds to three-dimensional imaging of a spatial distribution of the particle ensemble.

For a three-dimensional representation, this method is in this regard refined, a third gradient field being generated along a third direction after the second step, steps 1 to 4 being repeated with a number of modified second gradient fields, and a three-dimensional distribution of the transverse magnetization being determined from the set of measurement signals obtained and being output. Preferably, in both methods, the respective spatial directions x, y and z are mutually perpendicular.

If, in the latter method, all three gradient fields are used for phase encoding before the data acquisition, then all three spatial directions are recorded by means of the phase. Overall, for a 3D image matrix of N×N×N image points, precisely as many measurement steps are required. On the other hand, the frequency distribution only contains information about the variation of the rotation properties for each voxel separately, so that firstly the achievable resolution is no longer limited by the particle dispersion, and secondly the environmental parameters such as temperature, molecule concentrations etc. can be spatially resolved.

Independently of this, the possibility remains for the present method of sampling the frequency space with a system in polar coordinates for the image reconstruction.

In a preferred configuration, a spatially resolved density distribution of the small particles is determined from the determined distribution of the transverse magnetization and is output. With position encoding of the average asynchronous rotation frequencies by an applied magnetic gradient field, the spatially resolved density distribution of the small particles is obtained directly from the amplitudes of the corresponding frequency components of the transverse magnetization.

In order to obtain a high signal yield, and particularly in order to achieve the above-described phase encoding for multidimensional imaging, the magnetizations of the small particles are expediently set in a rotation synchronous with the rotating magnetic field before the measurement by means of a short-term magnetic refocusing field. Immediately after this refocusing field is switched off, all the magnetizations then rotate in phase. The measurement signal of the superimposed transverse magnetization is maximal. By applying a short-term gradient field it is then possible, starting from this situation, to carry out the phase encoding. Likewise starting from this situation in an external magnetic field applied for asynchronous rotation, the convergence of the individual magnetizations due to the different chemical embedding or environment can be observed. With an increasing time period, the individual asynchronously rotating magnetizations of the small particles dephase.

The refocusing field may be generated either by a short-term increase of the magnetic field strength and/or a short-term reduction of the rotation frequency of the rotating magnetic field. As an alternative, it is possible to generate a short-term magnetic offset field switched on in addition.

In another advantageous configuration, the refocusing field is generated by selectively setting only the magnetizations of small particles of equal rotation properties in a synchronous rotation. In this case, use is made of the fact that the described critical frequency $\Omega_C$, which describes the transition between synchronous and asynchronous rotation, is also dependent on the volume or shape of the small particles. This dependency means on the one hand that the measurement signal of the recorded superimposed transverse magnetization is degraded with an increasing bandwidth of the small particle variation. If, on the other hand, the refocusing pulse is generated in such a way that only small particles with the same rotation properties are set in a synchronous rotation, then only these contribute to the superimposed transverse magnetization. The magnetizations of the other small particles, conversely, are stochastically distributed. Overall, an improvement of the recorded measurement signal is obtained in this way without having to reduce the bandwidth of the sizes of the small particles used, which may entail high costs.

In a particularly advantageous configuration variant, a rotating magnetic gradient field with its gradient profile is spatially shifted over the measurement volume for phase encoding, the field strength in the gradient profile increasing beyond a value which leads to excitation of an asynchronous rotation of the small particles, at least up to a value which leads to the excitation of a synchronous rotation of the small particles. This takes into account the fact that the field dependency of the asynchronous rotation drift behaves non-linearly, and that the magnetic small particles typically have a scatter in their particle properties.

If, as already described above, phase encoding is carried out by applying a magnetic gradient field for a particular time period, then the nonlinear dependency of the asynchronous rotation drift on the field strength, and the scatter of the particle properties, lead to undesired degradation of the image resolution. The imposed local phase angle is blurred. Small particles differing in their particle properties at the same location experience a different imposed phase. In particular, the phase profile over the measurement volume also differs.

If, instead of this, a rotating magnetic gradient field is shifted over the measurement volume for phase encoding of the gradient profile, and if the field strength in the gradient profile increases at least up to a value at or beyond which the small particles are excited in synchronous rotation, then the same phase profile is imposed on all the small particles over the measurement volume. Different particle types merely have a globally consistent phase offset from one another. This phase difference, however, does not compromise the linearity of the imaging. Rather, the phase difference contains additional information about particle distribution or other local differences, and this can be evaluated separately.

To this end, for example, two particle types (or two identical particles in a different environment), which have a different critical field strength for a given rotation rate of the gradient field, are observed. When the critical field strength is fallen below, the synchronous rotation is broken. In the region of the gradient field with high field strength, both particle types rotate synchronously with the rotation of the external field. If the gradient profile is then shifted spatially over the measurement volume, then the critical field strength is first fallen below for the particle type with the higher critical field strength, and this only happens with a time lag for the particle type with the lower critical field strength. In other words, the two particle types experience a temporally offset switching off of the rotation field. The time offset is dependent on the shape of the gradient profile and on the displacement rate. Over the measurement volume, or in the encoding direction, both particle types experience imposition of the same phase profile. The phases of the two particles differ globally by a fixed phase difference.

Shifting the described gradient profile of a rotating magnetic field therefore makes it possible, independently of particle properties and the chemical environment, to carry out position encoding by imposing a phase profile. The imposition of a so-called spatial harmonic, with a spatial wavelength along which the phase angle varies by 180°, leads to determination of the corresponding Fourier coefficient during measurement of the macroscopic transverse magnetization. By corresponding repetition of the phase encoding with a different displacement rate, the Fourier coefficients of the other harmonics can be determined, so that the full Fourier encoding is obtained. In the $N^{th}$ phase encoding step corresponding to N image points in the encoding direction, the direction of the magnetization vector in the measurement volume rotates N/2 times about its own axis. For three-dimensional imaging, it is correspondingly necessary to carry out N×N×N steps.

The described method combines refocusing with the imposition of a phase. When travelling over the measurement volume with the gradient profile of the rotating magnetic gradient field, field strengths corresponding to refocusing are effective which excite the small particles in a synchronous rotation. With further displacement, the field strength falls below the critical value, so that the regime of asynchronous rotation is subsequently reached.

Preferably, the field strength in the gradient profile increases from essentially zero. In practice, however, there is a lower limit on the field strength beyond which only minimal encoding errors still arise.

The shift of the gradient profile is expediently carried out by individual driving of individual coils in a coil array. In particular, time-offset switching of the individual coils on and off is carried out for this purpose along the encoding direction.

For particles with Néel relaxation, the size is effectively the crucial selection criterion. The ratio of the magnetic moment of the particle and its friction term is generally critical. For massive particles with magnetization fixed in the lattice, the friction term is independent of the size and depends only on the form factor. Through suitable selection of the field strength and/or the rotation frequency of the refocusing field, particles with the same rotation properties, i.e. particles having the same rotation drift with an equal field strength and equal rotation frequency, are accordingly selected.

Selective refocusing of this type may, for example, be achieved by a rotating magnetic field whose rotation axis revolves on a trajectory. In this case refocusing takes place only for very specific particles with an integer divider ratio. This is because only particles which have a 1/n-fold rotation frequency, relative to the rotation of the refocusing field (n: integer), return into the original position after the end of the application of the 3D rotation field. In this way, highly selective refocusing pulses can be achieved. The signal selection is carried out using a suitable low- or bandpass filter.

The bandwidth of the recorded transverse magnetization may preferably be reduced by corresponding adjustment of the field strength and/or the rotation frequency of the rotating magnetic field and/or of the gradient field (slope, field strength). The signal acquisition is thereby improved.

In an expedient configuration, the or each magnetic gradient field is generated in such a way that there is a linear position dependency of the average rotation frequency of the magnetizations. In other words, the magnetic gradient field is as it were adjusted inversely to the given dependency of the average rotation frequency on the field strength, so that conversely there is a linear dependency of the average rotation frequency on the position. This allows more rapid image reconstruction.

The superimposed transverse magnetization may in principle be acquired by means of suitable physical measurement methods. In particular, inductive acquisition by means of a suitably formed and oriented measurement coil is suitable.

The fact that the field strengths required for the new magnetic particle imaging method lie in the millitesla (mT) range opens up a unique possibility for physiological image allocation, namely combining the method provided here with a low-field nuclear magnetic resonance method. This is because the gradient field used for the image encoding, which can be generated using air coils, can be switched off arbitrarily. The procedure used for the previous method of imaging by means of magnetic small particles, conversely, requires an enormously strong magnetic gradient field which cannot be switched off because of the neodymium permanent magnets which are required. Combination with a nuclear magnetic resonance method is therefore ruled out.

Since a method for imaging by means of magnetic small particles images exclusively contrast agent, however, the physiological image allocation is indispensable particularly in the medical field. In the present case, this physiological image allocation can now be achieved in particular by the parallel provision of a low-field nuclear magnetic resonance method. The method provided here for imaging from the asynchronous rotation of magnetic small particles and the low-field nuclear magnetic resonance method can readily be implemented for this purpose in a single apparatus. This is because the low-field nuclear magnetic resonance method also works at field strengths which can be generated using conventional electromagnets, in particular with air coils. For a medical examination, the imaging of the low-field nuclear magnetic resonance method may be used by means of imaging organs, tissues, etc. for physiological allocation of the recorded distribution of the contrast agent with magnetic small particles.

With respect to the device, the stated object is achieved according to the invention by a device for imaging by means of magnetic small particles, which comprises a magnetic field generator for generating a magnetic field rotating about a longitudinal axis, a measuring instrument for recording the frequency components of the superimposed transverse magnetization, a control device which is adapted to drive the magnetic field generator according to the method described above and to convert the recorded frequency components into a spatially resolved distribution of the transverse magnetization of the small particles, and an output device for output of the distribution obtained.

The output device may in this case provide the obtained measurement data, or the obtained spatially resolved distribution, for example in the form of digital data, as memory information on data media, via networks or the like, or it may directly be an information medium on which the obtained spatially resolved distribution is represented.

In an expedient configuration, the measuring instrument comprises an induction coil aligned parallel with the longitudinal axis. This may, in particular, be configured as a solenoid coil having a plurality of parallel windings. By means of such an induction coil, the superimposed transverse magnetization is then recorded directly as the measurement signal. Preferably, the measuring instrument is formed by an array of detector coils, each coil segment of the array having its own reception channel. Since each coil segment lies at a different spatial position, coarse spatial encoding is already obtained owing to the spatially limited reception profile of an individual coil segment. In this way, the image encoding can be carried out with correspondingly few phase encoding steps, so that the image acquisition can be accelerated. For each coil segment, as it were an incomplete data set is obtained (owing to the missing phase encoding), from which in principle a single complete data set can then be reconstructed by using the additional information about the array. For the image generation, the data need to be Fourier-transformed. The reconstruction may in this regard be carried out before the transformation with the aid of the additional information about the array, or after the transformation by corresponding deconvolution.

In order to suppress the induction voltages or induction currents in the measurement signal, which are generated by the external magnetic field, the input signal of the magnetic field generator is preferably coupled in antiphase with the coil output signal. This coupling may, for example, be carried out inductively by means of a transformer or the like.

Preferably, active negative feedback is also used in order to improve the measurement method. In this case, the noise components in the reception chain are recorded in a calibration measurement. These noise components are then injected directly into the reception chain with the opposite sign during the actual measurement. For this purpose, a transformer or generally an RF transmitter is advantageously provided. The injection signal is, in particular, generated by means of a digital/analog converter.

In order to remove the higher frequencies of the superimposed transverse magnetization, which are due to rotation flips relative to the external rotating magnetic field and do not contribute to the measurement signal, a low- or bandpass filter is advantageously provided. By a lowpass filter, frequencies below the rotation frequency of the external rotating magnetic field are selected. A bandpass filter also makes it possible to filter out a low-frequency noise components. Such low-frequency noise components may, for example, occur as a result of periodic refocusings carried out before each measurement sequence.

In an advantageous configuration, the magnetic field generator comprises normally conducting coil pairs, which are configured in order to generate a rotating magnetic field with a field strength of between 0.1 mT and 100 mT and a rotation frequency of between 1 kHz and 1 MHz. Such coils are to be regarded as relatively favorable. The desired magnetic fields may be generated using air coils or using water-cooled coils.

In a simple embodiment, the coil pairs are formed as Helmholtz coil pairs oriented mutually orthogonally. In this way, a rotating external magnetic field with high homogeneity can be generated in a straightforward way.

In order to generate the gradient field, the magnetic field generator may be driven accordingly. In an advantageous refinement, at least one gradient coil is provided for generating a magnetic gradient field in the direction transverse to the rotating magnetic field with a field strength of between 0.1 mT and 100 mT. In order to generate a linear gradient, a Golay biplanar coil is preferred in particular. In contrast to nuclear magnetic resonance, the primary magnet which makes a cylindrical geometry compulsory there is obviated. For the measurement device described here, the biplanar embodiment is therefore the most advantageous embodiment of a Golay coil.

In a particularly advantageous configuration, the device for imaging by means of magnetic small particles is combined with a device positioned relative thereto for carrying out a low-field nuclear magnetic resonance method. In this way, physiological image allocation can be carried out.

Further advantages may be logically attributed from the described method to the device provided here.

Exemplary embodiments of the invention will be explained in more detail with the aid of a drawing, in which:

FIG. 1 represents the profile of the average rotation frequency of the magnetization of a magnetic small particle relative to the rotation frequency of an external magnetic field. The profile of curve a corresponds to a lower field strength than the profile of curve b.

It can be seen that the average rotation frequency of the magnetization of a magnetic small particle rotates synchronously with the external rotation frequency up to a critical frequency $\Omega_C$. Above the critical frequency $\Omega_C$, the average rotation frequency is reduced relative to the external rotation frequency. The magnetization, or the small particle itself, then rotates with an average rotation frequency asynchronously relative to the external field. The fact that the critical frequency $\Omega_C$, and therefore also the average rotation drift relative to the external magnetic field, show a field dependency can be used for imaging.

Figure 1:
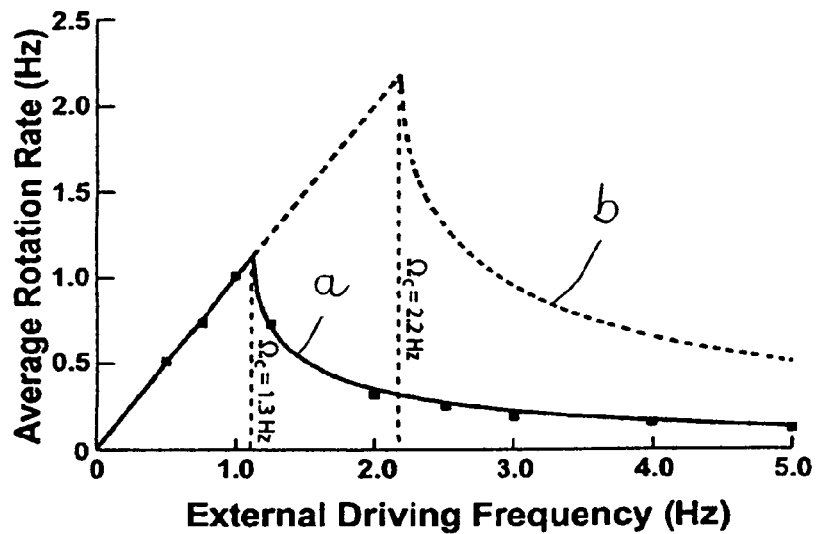
FIG. 1 shows the frequency response of the average rotation frequency of the magnetization of a small particle relative to the rotation frequency of an external magnetic field.

The curves a and b in FIG. 1 can likewise be used to illustrate clearly the dependency of the average rotation drift relative to a modified chemical embedding or environment. For example, the curve profile a would result during mechanical rotation of the small particle in a medium of higher viscosity relative to the curve profile b. For the same field strength, the small particle can already no longer follow the field in a highly viscous medium with a lower external rotation frequency.

Figure 2:
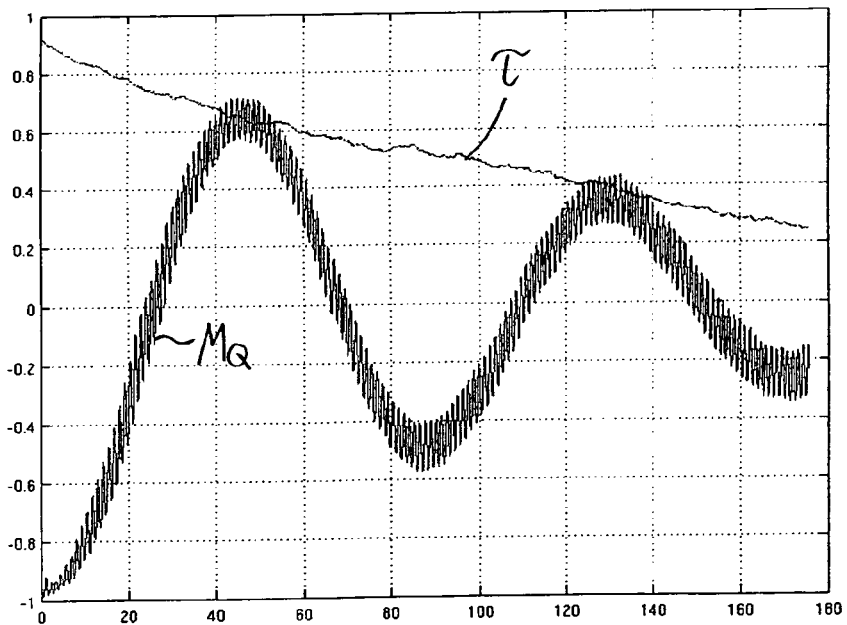
FIG. 2 shows the profile of the superimposed transverse magnetization after a refocusing pulse and FIG. 3 schematically shows a suitable device for imaging by means of magnetic small particles.

FIG. 2 shows the time profile of the measured superimposed transverse magnetization $M_Q$ after a refocusing pulse by means of a briefly applied external magnetic field. After the refocusing field is switched off, the individual magnetizations of the small particles rotate in phase in a correspondingly applied rotating external magnetic field. The superimposed signal of the transverse magnetization $M_Q$ has a maximum value. In accordance with the rotation frequency of the external magnetic field, the sum signal represented is obtained. Owing to variations of the particle size and/or particle shape, as a result of field inhomogeneities and as a result of different chemical environments, the individual magnetizations increasingly dephase. The amplitude of the measurement signal falls with a relaxation time $\tau$. By a rotation direction reversal of the external magnetic field, an echo could be generated in the measurement signal in a similar way to the spin-echo known from the nuclear magnetic resonance method.

Figure 3:
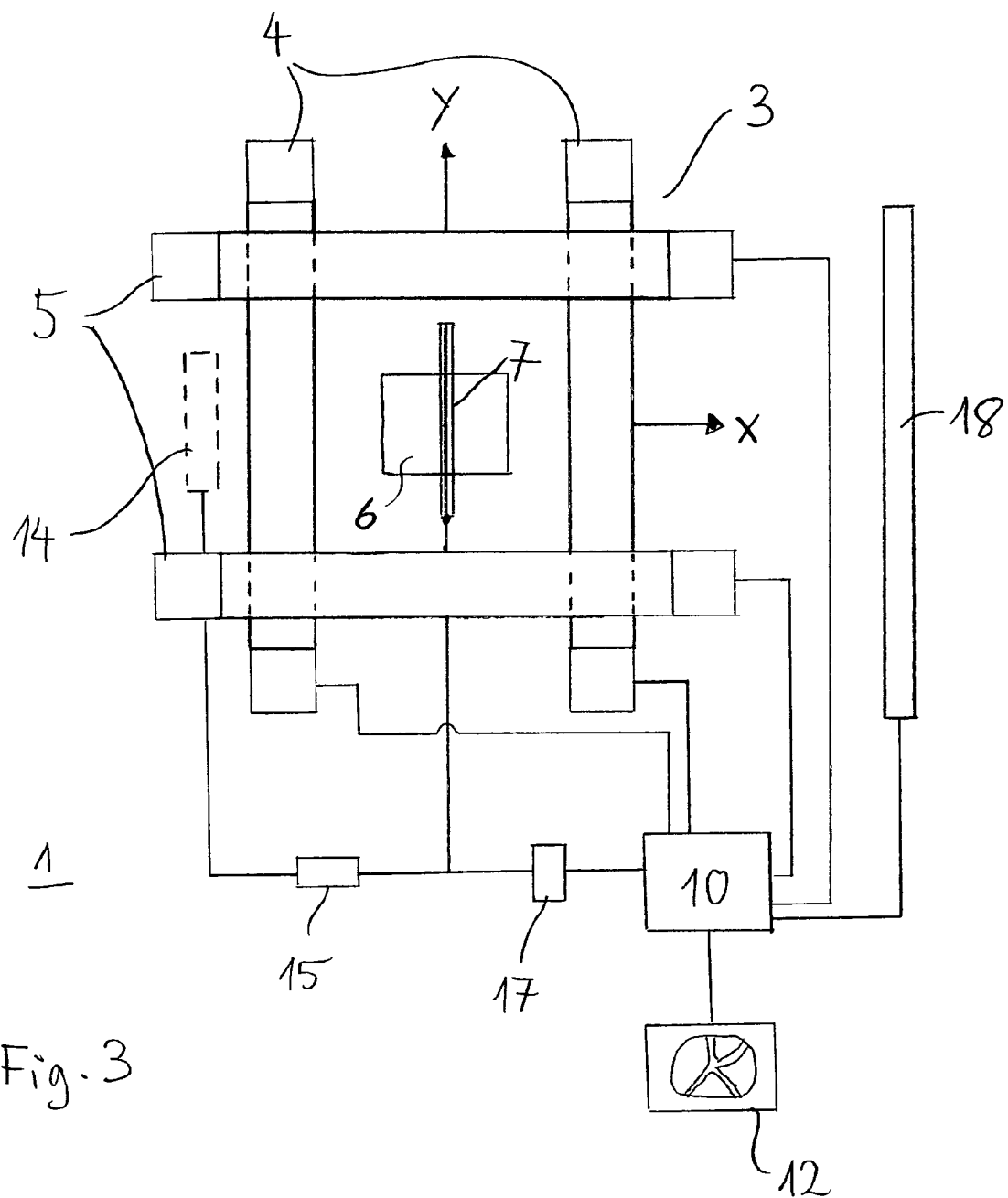

FIG. 3 schematically represents a device 1 for imaging by means of magnetic small particles. To this end, the device 1 comprises a magnetic field generator 3 which is formed by two Helmholtz coil pairs 4 and 5 positioned orthogonally with respect to one another. The Helmholtz coil pair 4 generates a homogeneous magnetic field here in the x direction. The Helmholtz coil pair 5 generates a homogeneous magnetic field orthogonal thereto in the y direction. By means of sinusoidal driving of the corresponding coils, an external magnetic field rotating about the z axis can be generated.

In the internal space between the Helmholtz coil pairs 4, 5, a measurement volume 6 is formed in which, for example, a spatial distribution of a contrast agent containing magnetic small particles is intended to be recorded. To this end, the generated external magnetic field rotates with a correspondingly predetermined frequency and a correspondingly selected field strength in such a way that the individual magnetizations of the small particles rotate asynchronously with the external field. The superimposed transverse magnetization, oriented perpendicularly to the z axis, of the particle ensemble contained in the measurement volume 6 is recorded inductively by means of a measuring instrument 7. The measuring instrument 7 is a solenoid coil aligned parallel with the z axis.

In order to drive the Helmholtz coils 4, 5 and in order to record the measurement signal received by the measuring instrument 7, a control device 10 is provided. In addition to the rotating magnetic field, by means of appropriate driving of the Helmholtz coils 4, 5 a magnetic gradient field is generated which is used for position encoding of the frequency components of the superimposed transverse magnetic field. As an alternative, gradient coils for generating in particular linear gradients may be provided for all three spatial directions. So-called Golay biplanar coils are particularly suitable for this.

By means of the control device 10, an image of the spatial distribution of the magnetic small particles or an image of properties of their chemical environment can be generated by appropriate driving of the magnetic coils. For example, a refocusing magnetic field for phase alignment of the individual magnetizations may be generated and subsequently sampled to form a two-dimensional image of the frequency space by a Cartesian system, for which purpose phase encoding is respectively carried out by varying the gradient fields.

In order to suppress inductive voltages or inductive currents, which are due to the external magnetic fields, a negative feedback pickup 14 is arranged between the coils of the coil pair 5. Its output signal is fed back negatively by means of a coupling unit 15 (for example inductively) to the output signal of the measuring instrument 7. A low pass filter 17 is furthermore provided for selecting average asynchronous rotation frequencies which are reduced relative to the rotation frequency of the external magnetic field.

The control device 10 is connected to an imaging device which, for example, is formed as an information medium which displays the image determined. A device 18 for imaging by means of the low-field nuclear magnetic resonance method is combined for physiological image allocation.

LIST OF REFERENCES a) average rotation rate (low field)
b) average rotation rate (high field)
$\tau$ transverse relaxation
$M_Q$ transverse magnetization
1 device
3 magnetic field generator
4 Helmholtz coil pair, x direction
5 Helmholtz coil pair, y direction
6 measurement volume
7 measuring instrument
10 control device
12 imaging device
14 negative feedback pickup
15 coupling unit
17 lowpass filter
18 low-field nuclear magnetic resonance device

The invention claimed is:
1. A method for imaging from a distribution of magnetic small particles, the method comprising:
  setting the magnetizations of the magnetic small particles in a rotation using an external magnetic field of a field strength and rotation frequency rotating about a longitudinal axis (z), wherein the rotation of the magnetizations of the magnetic small particles is asynchronous with respect to the external magnetic field, wherein an asynchronous average rotation frequency dependent on the field strength results for a magnetic small particle ensemble of the magnetic small particles,
  applying a magnetic gradient field to impose a position dependency on the asynchronous average rotation frequency of the magnetic small particle ensemble,
  recording the frequency components of the superimposed transverse magnetization ($M_Q$) of the magnetic small particle ensemble using a coil aligned parallel with the longitudinal axis (z) and using a low pass filter to select average asynchronous rotation frequencies that are reduced relative to the rotation frequency of the external magnetic field, converting the recorded frequency components into spatially resolved distribution of the transverse magnetization ($M_Q$) of the magnetic small particle ensemble, and determining the spatially resolved distribution of the superimposed transverse magnetization ($M_Q$) using the recorded frequency components and outputting the spatially resolved distribution.

2. The method as claimed in claim 1, wherein the magnetic gradient field is generated for frequency encoding during the recording of the frequency components of the transverse magnetization ($M_Q$).

3. The method as claimed in claim 1, wherein the magnetic gradient field is generated for a predetermined time period for phase encoding before recording the frequency components of the transverse magnetization ($M_Q$).

4. The method as claimed in claim 3, wherein, after the magnetic gradient field is switched off, a second equal magnetic gradient field of opposite sign is generated with the same time period, and wherein the spatially resolved distribution of the transverse magnetization ($M_Q$) is subsequently determined in a plane perpendicular to the profile of the gradient.

5. The method as claimed in claim 1, wherein the magnetic gradient field is generated by spatial variation of the field strength of the rotating magnetic field.

6. The method as claimed in claim 1, wherein the frequency components of the transverse magnetization ($M_Q$) are recorded several times for different magnetic gradient fields.

7. The method as claimed in claim 1, wherein:
a first magnetic gradient field is generated along a first direction in a first step for a time period,
a second magnetic gradient field is generated along a second direction in a second step,
the frequency distribution of the transverse magnetization ($M_Q$) is recorded in a third step,
steps one to three are repeated with a number of modified first magnetic gradient fields in a fourth step, and
a two-dimensional distribution of the transverse magnetization ($M_Q$) is determined from the set of measurement signals obtained.

8. The method as claimed in claim 7, wherein:
a third magnetic gradient field is generated along a third direction after the second step,
steps one to four are repeated with a number of modified second magnetic gradient fields, and
a three-dimensional distribution of the transverse magnetization ($M_Q$) is determined from the set of measurement signals obtained.

9. The method as claimed in claim 1, wherein the magnetizations of the small particles are set in a rotation synchronous with the rotating magnetic field before the measurement using a short-term magnetic refocusing field.

10. The method as claimed in claim 9, wherein the refocusing field is generated by selectively setting the magnetizations of small particles of equal rotation properties in a synchronous rotation.

11. The method as claimed in claim 1, wherein a rotating magnetic gradient field with its gradient profile is spatially shifted over the measurement volume for the phase encoding, and wherein the field strength in the gradient profile increases beyond a value which leads to excitation of an asynchronous rotation of the small particles, at least up to a value which leads to the excitation of a synchronous rotation of the small particles.

12. The method as claimed in claim 11, wherein the phase encoding is repeated several times with a modified displacement rate for the imaging.

13. The method as claimed in claim 1, wherein the rotating magnetizations of the small particles are brought into phase by a rotation direction reversal of the rotating magnetic field.

14. The method as claimed in claim 1, wherein a linear position dependency of the average rotation frequency is generated using each magnetic gradient field.

15. The method as claimed in claim 1, wherein imaging using a low-field nuclear magnetic resonance method is simultaneously carried out for image allocation.

16. A device for imaging using magnetic small particles, the device comprising:
a magnetic field generator configured to generate an external magnetic field of a field strength and rotation frequency rotating about a longitudinal axis (z) to set the magnetizations of the magnetic small particles in a rotation, wherein the rotation of the magnetizations of the magnetic small particles is asynchronous with respect to the external magnetic field, wherein an asynchronous average rotation frequency dependent on the field strength results for a magnetic small particle ensemble of the magnetic small particles, and to apply a magnetic gradient field to impose a position dependency on the asynchronous average rotation frequency of the magnetic small particle ensemble,
a measuring instrument configured to record the frequency components of the superimposed transverse magnetization ($M_Q$) of the magnetic small particle ensemble,
a control device configured to drive the magnetic field generator and to convert the recorded frequency components into a spatially resolved distribution of the transverse magnetization ($M_Q$) of the magnetic small particle ensemble, and
an output device configured to output the spatially resolved distribution.

17. The device as claimed in claim 16, wherein the measuring instrument comprises a number of induction coils aligned parallel with the longitudinal axis (z).

18. The device as claimed in claim 17, wherein the input signal of the magnetic field generator is coupled in antiphase with the coil output signal.

19. The device as claimed in claim 16, wherein the magnetic field generator comprises conducting coil pairs, which are configured in order to generate a rotating magnetic field with a field strength of between 0.1 mT and 100 mT and a rotation frequency of between 1 kHz and 1 MHz.

20. The device as claimed in claim 16, combined with a device positioned relative thereto and configured to carry out a low-field nuclear magnetic resonance method.

* * * * *